United States Patent [19]
Hemmerling et al.

[11] Patent Number: 5,348,684
[45] Date of Patent: Sep. 20, 1994

[54] ORGANOSILYLALKYL OR ORGANOSILYLALKENYL COMPOUNDS, PROCESS FOR PREPARING THEM AND THEIR USE IN LIQUID-CRYSTALLINE MIXTURES

[75] Inventors: Wolfgang Hemmerling, Sulzbach; Hans-Rolf Dübal, Königstein/Taunus; Claus Escher, Mühltal; Gerhard Illian, Frankfurt am Main, all of Fed. Rep. of Germany; Yoshio Inoguchi, Tokyo, Japan; Ingrid Müller, Hofheim am Taunus, Fed. Rep. of Germany; Mikio Murakami, Königstein/Taunus, Fed. Rep. of Germany; Dieter Ohlendorf, Liederbach, Fed. Rep. of Germany; Rainer Wingen, Hattersheim am Main, Fed. Rep. of Germany

[73] Assignee: Hoechst Aktiengesellschaft, Frankfurt am Main, Fed. Rep. of Germany

[21] Appl. No.: 932,644

[22] Filed: Aug. 20, 1992

Related U.S. Application Data

[63] Continuation of Ser. No. 393,386, Aug. 11, 1989, abandoned.

[30] Foreign Application Priority Data

Aug. 13, 1988 [DE] Fed. Rep. of Germany ....... 3827600

[51] Int. Cl.$^5$ ................. C09K 19/34; C09K 19/52; C09K 19/20; C07F 7/04
[52] U.S. Cl. .................. 252/299.61; 252/299.01; 252/299.63; 252/299.64; 252/299.65; 252/299.66; 252/299.67; 556/400; 556/413; 556/424; 556/427; 556/436; 556/437; 556/438; 556/440; 556/441; 556/445; 556/453; 556/454
[58] Field of Search ............... 252/299.1, 299.4, 299.5, 252/299.61, 259.63, 299.65, 299.66, 299.67; 556/400, 407, 413, 424, 427, 436, 437, 438, 440, 441, 445, 453, 454

[56] References Cited

U.S. PATENT DOCUMENTS

| | | |
|---|---|---|
| 4,316,041 | 2/1982 | Totten et al. |
| 4,367,924 | 1/1983 | Clark et al. .................. 359/103 |
| 4,678,283 | 7/1987 | Kreuzer et al. |
| 4,730,904 | 3/1988 | Pauluth et al. ................ 252/299.4 |
| 5,106,530 | 4/1992 | Haas et al. .................. 252/299.6 |
| 5,158,702 | 10/1992 | Haas et al. .................. 252/299.6 |
| 5,210,247 | 5/1993 | Häberle et al. ............... 556/413 |
| 5,217,645 | 6/1993 | Iwaki et al. ................ 252/299.61 |
| 5,277,838 | 1/1994 | Haas et al. ................ 252/299.01 |

FOREIGN PATENT DOCUMENTS 1-144491 6/1989 Japan.

*Primary Examiner*—Shean Wu
*Attorney, Agent, or Firm*—Curtis, Morris & Safford

[57] ABSTRACT

The novel silylalkyl or silylalkenyl compounds correspond to the general formula (I)

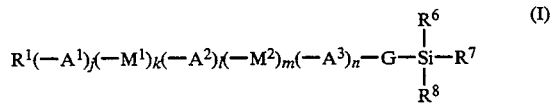

Here the symbols $A^1$, $A^2$, $A^3$ denote aromatic or heteroaromatic molecular units such as 1,4-phenylene or pyrimidine-2,5-diyl which are combined via a single bond (for k, m=0) or via functional groups $M^1$, $M^2$ such as CO—O or $CH_2$—O; j, k, l, m, n are zero or 1 (j+l+n=2 or 3). The radicals $R^2$, $R^3$, $R^4$, $R^5$ are hydrogen or alkyl/alkenyl, cycloalkyl, and the radicals $R^6$, $R^7$, $R^8$ have a comparable meaning (hydrogen); $R^1$ is alkyl/alkenyl or one of the substituents known from LC chemistry such as an α-haloalkanoic radical. In some cases compounds have wide and polymorphous liquid crystalline phases.

11 Claims, No Drawings

ORGANOSILYLALKYL OR ORGANOSILYLALKENYL COMPOUNDS, PROCESS FOR PREPARING THEM AND THEIR USE IN LIQUID-CRYSTALLINE MIXTURES

This application is a continuation of application Ser. No. 07/393,386, filed Aug. 11, 1989 now abandoned.

BACKGROUND OF THE INVENTION

The unusual combination of anisotropic and fluid behavior of liquid crystals has resulted in their use in a multiplicity of electro-optic switching and indicating devices. In this connection, use may be made of their electrical, magnetic, elastic and/or thermal properties to produce changes in orientation. Optical effects can then be achieved, for example, with the aid of birefrigence, of the incorporation of dichroically absorbing dyestuff molecules ("guest-host mode") or of light scattering.

To fulfill the continuously increasing practical requirements in the various fields of application, there is a constant need for novel improved liquid-crystal ("Liquid-Crystal") mixtures and consequently, also for a multiplicity of mesogenic compounds having a wide variety of structures. This is the case both for those fields in which nematic LC phases (for example TN="twisted nematic", STN="supertwisted nematic", SBE-"supertwisted birefringence effect", ECB="electrically controlled birefrigence") are used and also for those involving smectic LC phases (for example, ferroelectric, electroclinic).

Many of the compounds which are suitable for LC mixtures can be described by a construction principle (building system) (see, for example, J. Am. Chem. Soc. 108, 4736 (1986), structure I; Science 231, 350 (1986), FIG. 1A; J. Am. Chem. Soc. 108, 5210 (1986), FIG. 3), in which nuclei of cyclic compounds—aromatics, heteroaromatics, but also saturated ring systems—are linked to straight—chain alkyl side chains or alkyl side chains which are substituted in the chain by small groups (for example methyl, chlorine) and are consequently branched. Compounds which have a terminal silyl-substituted alkyl chain as a substructure are known, for example, from EP-A-0,136,501, DE-A-3,521,201 and 3,601,742. In these molecules, the Si atom has readily hydrolyzable substituents which are said to enable these compounds, in particular, to produce a homeotropic orientation of the liquid-crystalline phases on the surface. A liquid-crystalline behavior of the compounds is not reported, only their use as components of liquid-crystalline dielectrics.

SUMMARY OF THE INVENTION

The object of the present invention is to provide novel, chemically stable and mesogenic silicon compounds which are not hydrolyzable in the above sense and which can be combined with many other components to form LC mixtures. The compounds defined below achieve this object:

Liquid-crystalline silylalkyl or silylalkenyl compounds of the general formula (I)

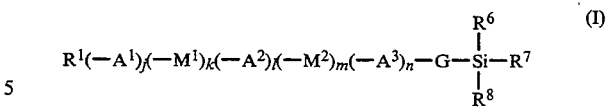

in which $R^1$ denotes straight-chain or branched alkyl or alkenyl (with or without asymmetrical carbon atom) containing 2 to 16 carbon atoms, it also being possible for one or two nonadjacent —$CH_2$— groups to be substituted by —O—, —S—, —CO—, —CO—O—, —O—CO— or —O—CO—O— and for hydrogen to be replaced by fluorine, or one of the following radicals $OCF_3$, $OCHF_2$

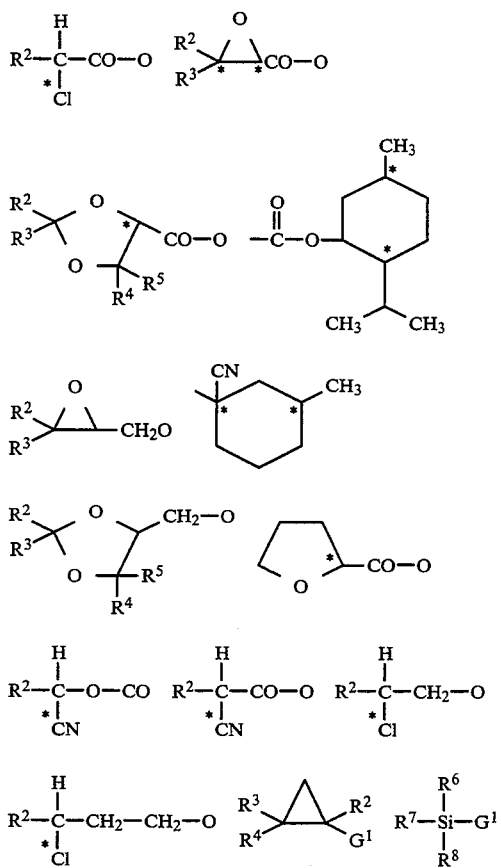

$A^1$, $A^2$, $A^3$ denote, identically or differently, 1, 4-phenylene in which 1 or 2 hydrogens may be replaced by fluorine, chlorine and/or CN, trans-1,4-cyclohexylene in which 1 or 2 hydrogens may be replaced by fluorine, chlorine, CN and/or $CH_3$, pyrazine-2,5-diyl, pyridazine-3,6-diyl, pyridine-2,5-diyl, pyrimidine-2,5-diyl, 1,3,4-thiadiazol-2,5-diyl, 1,3-dioxane-2,5-diyl, 1,3-dithiane-2,5-diyl, $M^1$, $M^2$ denote, identically or differently, CO—O, O—CO, CO—S, S—CO, $CH_2$—O, O—$CH_2$, C≡C, CH=CH, G, $G^1$ denotes straight-chain or branched alkylene containing 1 to 16 carbon atoms or alkenylene containing 2 to 16 carbon atoms, in which one or two nonadjacent —$CH_2$— groups may also be replaced by —O—, —S—, —O—CO—, —CO—O—, —S—CO— or —CO—S—, with the proviso that Si is bound only to a carbon which has hydrogen and/or carbon as adjacent atoms, R², R³, R⁴ denote hydrogen or a straight-chain or branched alkyl containing 1 to 16 or alkenyl containing 2 to 16 carbon atoms, in which a —CH₂— group may also be replaced by —O—, —CO—O— or —O—CO—, or cyclic alkyl containing 3 to 8 carbon atoms, R⁶, R⁷, R⁸ denote straight-chain or branched alkyl containing 1 to 16 carbon atoms or alkenyl containing 2 to 16 carbon atoms, in which one or two nonadjacent —CH₂— groups may also be replaced by —O—, —CO—O— or —O—CO—, with the proviso that it is bound only to a carbon which has hydrogen and/or carbon as adjacent atoms, or cyclic alkyl containing 3 to 8 carbon atoms, or, jointly with the Si, also

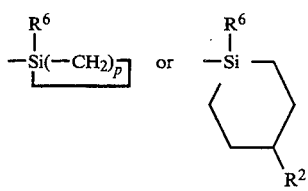

j,k,l,m,n denote 0 or 1,
p denotes 3 to 7
with the proviso that j+l+n=2 or 3.

DESCRIPTION OF THE PREFERRED EMBODIMENTS

Preferred are those compounds in which, in the general formula (I) the grouping $(-A^1)_j(-M^1)_k(-A^2)_l(-M^2)_m(-A^3)_n-$ denotes:

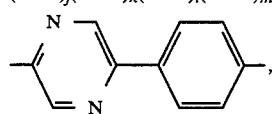

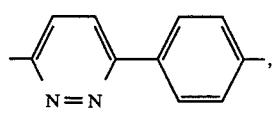

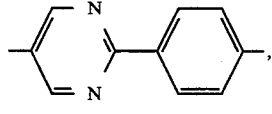

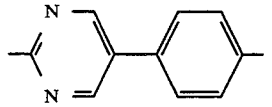

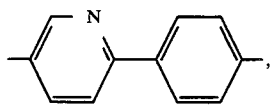

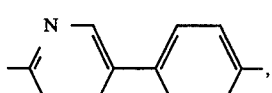

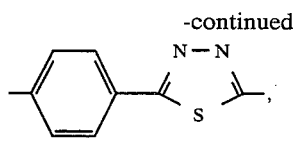

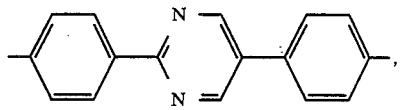

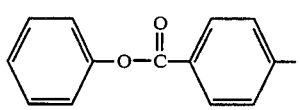

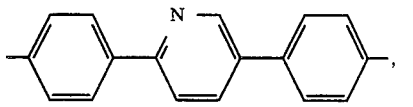

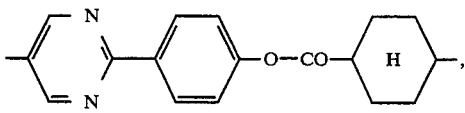

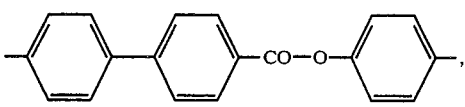

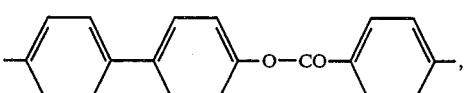

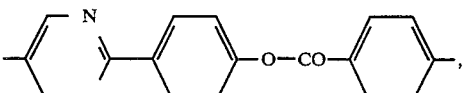

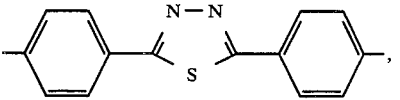

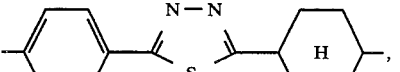

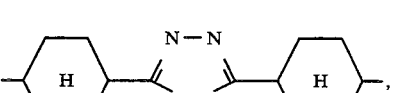

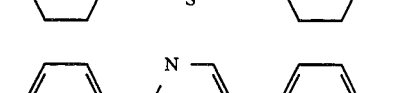

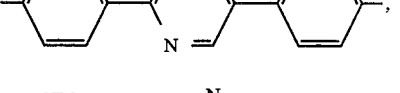

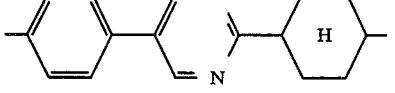

The novel silylalkyl or silylalkenyl compounds are chemically, photochemically and thermally stable and have a good mixing compatibility. Particularly preferred among the compounds of the general formula (I) are those in which at least one of the radicals $A^1$, $A^2$, $A^3$ denotes 1,4-phenylene and a further denotes pyrimidine-2,5-diyl.

A remarkable feature of the silyl compounds is that the substances have in some cases substantially lower melting points than the analogous alkyl compounds. In this case, the melting point is crucially dependent on the position of the dimethylsilyl group in the chain. It has emerged that particularly low melting points and wide liquid-crystalline phase ranges are obtained if the alkyl chains $G_7G^1$ and $R^7$ (see formula I) contain, independently of one another, between 2 and 8, particularly preferably, 4 to 5, —$CH_2$— units. For low melting points, an overall number of the —$CH_2$— unit in the silyl-substituted chain is advantageously between 7 and 12, and particularly favorable properties are obtained in chains having 8 or 9 -$CH_2$— chain members.

An outstanding feature of the silyl compounds are their good properties in mixtures. Thus, they not only have a good mixing compatibility but affect the melting point of mixtures in a special way. Thus, it was possible to observe, on the one hand, that, if the dimethyl-substituted compounds are used, categories of substance which are virtually insoluble at room temperature dissolve to an extent of 25 mol % and over in the liquid-crystalline mixture and at the same time result in some cases in an appreciable reduction in melting point and/or in a likewise advantageous shift of the crystalline on temperature to very low temperatures. These properties make the silyl compounds particularly important as constituents of liquid-crystalline mixtures. Especially silyl compounds of phenyl pyrimidine phenyl-benzoates are good examples for this fact. The chain length of the silyl components and the position of the dimethylsilyl group also play an important part in reducing the melting point. In this case, an overall number of the —$CH_2$— members in the silyl-substituted chain of between 7 and 12 is favorable, the overall length of 8 to 10 —$CH_2$— groups being preferred. At the same time, the chain members G and $R^7$ contain between 2 and 6 —$CH_2$— groups, preferably, however, 4 to 5 —$CH_2$— groups. The silyl compounds of the phenyl benzoates are particularly suitable for reducing the melting point. The use of silyl components offers further special advantages in addition to the favorable properties relating to solubility (inter alia, also of the dopants) and the lowering of both the crystallization temperature and of the melting point, especially for ferroelectric mixtures. Thus, it was possible to observe that the use of silyl compounds in some cases can result in a marked shortening of the switching times. A further advantage of silyl compounds is the fact that they induce a higher spontaneous polarisation as compared with unsubstituted compounds. It was also possible to demonstrate that silyl compounds produce a higher effective switching angle than the corresponding alkyl compounds and consequently, a better transmission in the clear state in the electro-optic switching element.

Preferred silyl components for increasing the effective switching angle are the phenyl benzoates and the 5-phenylpyrimidine-2-yl compounds.

A further achievement of the object set is a liquid-crystal mixture having a content of at least one liquid-crystalline compound, which mixture contains at least one compound of the general formula (I) as liquid-crystalline compound. The liquid-crystal mixtures are composed of 2 to 20, preferably 2 to 15 components, including at least one of the compounds claimed according to the invention. The other components are preferably selected from the known compounds having nematic, cholesteric and/or tilted smectic phases, which include, for example, Shiff's bases, biphenyls, terphenyls, phenylcyclohexanes, cyclohexylbiphenyls, pyrimidines, cinnamic acid esters, cholesterol esters, and various bridged, terminally polar, polynuclear esters of p-alkylbenzoic acids. In general, the liquid-crystal mixtures obtainable commercially already exist before the addition of the compound(s) according to the invention, as mixtures of a wide variety of components, at least one of which is mesogenic, i.e. as a compound which, in the form of a derivative or as a mixture with certain associated components, exhibits a liquid-crystal phase (= can be expected to form at least one enantiotropic (clearing point > melting point) or monotropic (clearing point < melting point) mesophase).

The liquid-crystal mixtures contain in general 0.01 to 70% by weight, in particular 0.05 to 50% by weight, of the compound(s) according to the invention.

The compounds according to the invention can be prepared by standard reactions known per se from mesogenic parent substances such as phenols of the general formula (II) where X=OH or O-alkali:

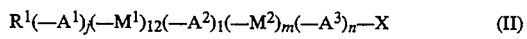

$$R^1(-A^1)_l(-M^1)_{12}(-A^2)_1(-M^2)_m(-A^3)_n-X \quad \text{(II)}$$

and the monofunctionally reactive silylalkyl or silylalkenyl compounds of the general formula (III):

$$\begin{array}{c} R^6 \\ | \\ Y-G-Si-R^7 \\ | \\ R^8 \end{array} \quad \text{(III)}$$

where Y=H, OH, Hal, OMes (=methylsulfonyloxy), OTos (=toluenesulfonyloxy), it being possible to assume the synthesis of these reaction components to be known.

Thus, for example, mesogenic hydroxyl or mercapto compounds may be combined with organosilylalkanols in the presence of triphenylphosphine/azodicarboxylic acid diesters (Mitsunobu reaction, for example in J. Chem. Soc. Perkin Trans. 1975, 461). The separately or intermediately produced alkali-metal or alkaline-earth salts of these mesogenic hydroxyl or mercapto compounds with halo-, toluenesulfonyloxy- or methylsulfonyloxyorganosilylalkyl or alkenyl compounds may also be reacted (Williamson reaction, for example in Patai, The Chemistry of the Ether Linkage, Interscience Publishers, New York 1967, pages 446–468).

Mesogenic carboxylic acids (X=COOH in formula (II)) may also be reacted with organosilylalkanols under condensation conditions (for example, in March, Advanced Organic Chemistry, 2nd Ed., McGraw-Hill Kogakuska Ltd., Tokyo 1977, pages 363–365) or, under the conditions of the Williamson reaction (X=COO-alkyl in formula (II)), with organosilylalkyl halides or -sulfonyl compounds. In the same way, this is also possible with mesogenic hydroxyl or mercapto compounds and organosilylalkanoic acids.

The organosilyl compounds necessary for the combination are prepared by methods known per se (for example, C. Eaborn et al. in Organometallic Compounds of the Group IV Elements, Vol. 1, Part 1, Dekker New York, 1968; E. Lukevics et al. in J. Organomet. Chem.

Libr. 5, 1 (1977) or R. Heumer et al., in Houben-Weyl Methoden der org. Chemie, E 18/2, page 685 ff, Thieme-Verlag Stuttgart-New York, 1986).

They may be prepared, for example, by reacting unsaturated Z-$C_nH_{2n-1}$ compounds (Z=Benzyloxy, TBDMS-oxy, Hal) with HSiR$^7$R$^8$Cl dialkylchlorosilanes in the presence of a noble-metal catalyst (for example, H$_2$PtCl$_6$ in isopropanol) and possibly in the presence of an inert organic solvent at temperatures between 0° and 150° C., the silane advantageously being used in excess. Subsequently thereto, the Z-$C_nH_{2n}$-SiR$^7$R$^8$-Cl chlorosilane produced is treated with an organometallic reagent such as R$^6$MgHal or R$^6$Li in a suitable inert organic solvent at temperatures between −78° C. and +100° C. In a further variant, Z-$C_nH_{2n}$-Hal can be converted into the Grignard compound and reacted with chlorosilanes of the formula ClSiR$^6$R$^7$R$^8$. Insofar as Z corresponds to a benzyloxy or TBDMS-oxy group, this group is converted to an OH group by standard methods (for example, W. Greene, Protective Groups in Organic Synthesis, Wiley, N.Y., 1981).

Furthermore, HSiR$^7$R$^8$Cl or ClSiR$^6$R$^7$R$^8$ silanes can be reacted with compounds of the type Z-$C_nH_{2n-1}$ or Z-$C_nH_{2n}$-Hal directly to form compounds of the general formula (I), provided Z does not have the meaning cited above but that of R$^1$(—A$^1$)$_i$(—M$^1$)$_k$(—A$^2$)$_l$(—M$^2$)$_m$(—A$^3$)$_n$.

The values of the spontaneous polarization P$_s$ [nC/cm$^2$], the optical switching time τ [μs], and the effective switching angle θ$_{off}$ [°] were determined for the ready-to-use ferroelectric liquid-crystal mixtures as follows:

The P$_s$ values are measured by the method of H. Diamant et al. (Rev. Sci. Instr., 28, 30, 1957) measuring cells having an electrospacing of 2 μm and stroked polyimide as orientation layer.

To determine τ and θ$_{off}$ the measuring cell is mounted on the revolving stage of a polarizing microscope between crossed analyser and polarizer.

By rotating the stage, the position of the stage with minimum light transmission is determined for the two switching states in the cell. The difference between the two positions on the revolving stage is equal to twice the effective angle of tilt.

The switching time τ is determined with the aid of a photodiode by measuring the rise time of the light signal from 10 to 90% signal amplitude. The switching voltage is composed of square-wave pulses and is ±10 V/μm.

The phase change temperatures are determined with the aid of a polarizing microscope on the basis of the textural changes during heating. The melting point, on the other hand, was determined with a DSC apparatus. The phase change temperatures between the phases nematic (N or N*),
smectic-C (S$_c$ or S$_c$*),
smectic-A (S$_A$ or S$_A$*) and
crystalline (X or K)

are specified in ° C. and the values are placed between the phase denotations in the phase sequence.

EXAMPLE 1

4-(Trimethylsilyl)butyl 4-(5-octyloxypyrimidin-2-yl)-phenyl ether

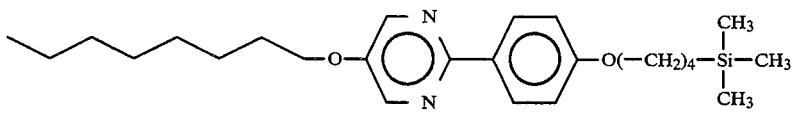

439 mg (3 mmol) of 4-(Trimethylsilyl)butan-1-ol and 901 mg (3 mmol) of 4-(5-n-octyloxypyrimidin-2-yl)phenol are added to the solution of 0.46 ml (3 mmol) of diethyl azodicarboxylate and 790 mg (3 mmol) of triphenylphosphine in 15 ml of dry tetrahydrofuran. After a reaction time of 15 h, the solvent is distilled off and the residue is purified chromatographically (SiO$_2$/CH$_2$Cl$_2$). After recrystallization from n-hexane, 790 mg of colorless crystals are obtained.

Phase sequence: K 68.5 S$_c$ 77.6 S$_A$ 77.6–78.3 I

The syntheses below are carried out as specified in Example 1 with appropriate quantity adjustment.

EXAMPLE 2

4-(Trimethylsilyl)butyl 4-(2-octyloxypyrimidine-5-yl)-phenyl ether

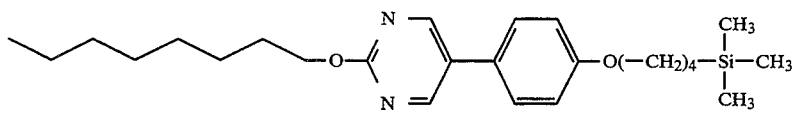

Phase sequence: K 70.3 I

EXAMPLE 3

4-(Trimethylsilyl)butyl 4-(2-octylpyrimidine-5-yl)phenyl ether

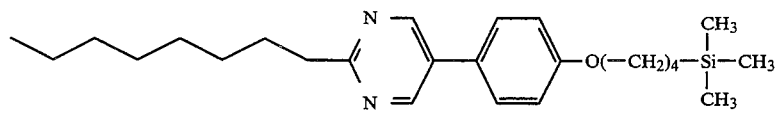

Phase sequence: K 61.8 I

EXAMPLE 4

4-(Trimethylsilyl)butyl
4-(5-octylpyrimidine-2-yl)phenyl ether

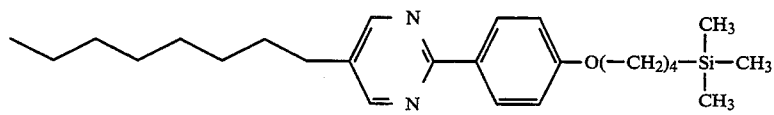

Phase sequence: K 52.9 S$_c$ (39.7) S$_A$ (43) I

EXAMPLE 5

4-(Ethyldimethylsilyl)butyl
4-(5-octyloxypyrimidin-2-yl)phenyl ether

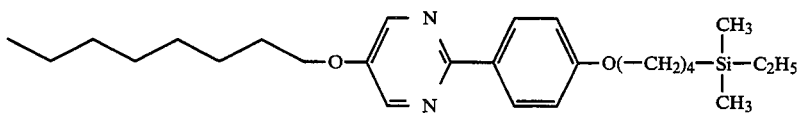

Phase sequence: K 49.4 S$_c$ 71 S$_A$ 71.3 I

EXAMPLE 6

4-(Ethyldimethylsilyl)butyl
4-(2-octyloxypyrimidin-5-yl)phenyl ether

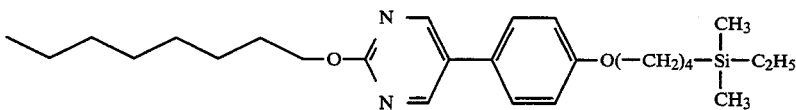

Phase sequence: K 63.3 I

EXAMPLE 7

4-(Ethyldimethylsilyl)butyl
4-(2-octylpyrimidin-5-yl)-phenyl ether

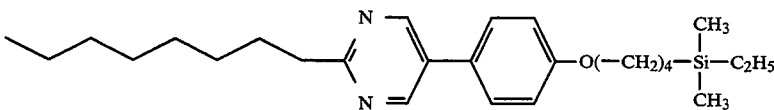

Phase sequence: K 50.9 I

EXAMPLE 8

4-(Ethyldimethylsilyl)butyl
4-(5-octylpyrimidin-2-yl)-phenyl ether

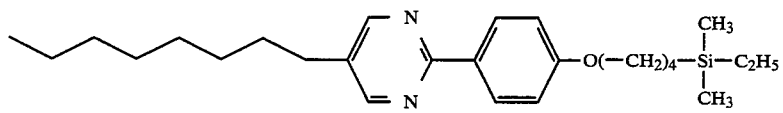

Phase sequence: K 35.2 S$_c$ (30.6) S$_A$ (32.3) I

EXAMPLE 9

4-(n-Butyldimethylsilyl)butyl
4-(2-octyloxypyrimidin-5-yl)-phenyl ether

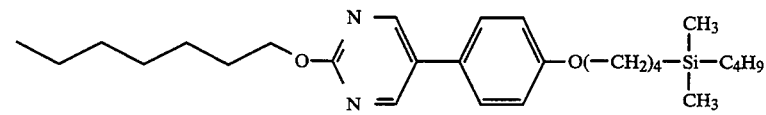

Phase sequence: K 35.8 I

EXAMPLE 10

4-(n-Butyldimethylsilyl))butyl
4-(2-octylpyrimidin-5-yl)phenyl ether

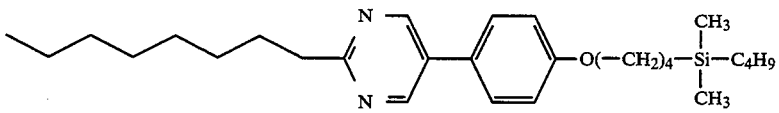

Phase sequence: K 25.4 I

EXAMPLE 11

4-(n-Butyldimethylsilyl)butyl
4-(5-octyloxypyrimidin-2-yl)phenyl ether

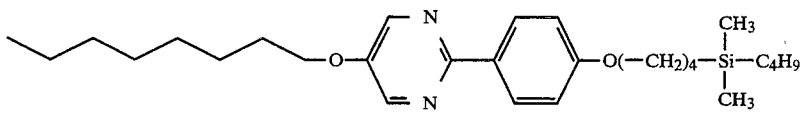

Phase sequence: K 16.5 $S_c$ 63.1 $S_A$ 64 I Compared therewith, the two following unsubstituted phenyl-pyrimidines have a much higher melting point: 5-octyloxy-2-(4-octyloxyphenyl)-pyrimidine has the phase sequence K 50,7 $S_c$ 92 $S_A$ 99 N 100 I, 5-octyloxy-2-(4-decyloxyphenyl)-pyrimidine has the phase sequence: K 50,2 $S_c$ 89 $S_A$ 99 I. The silyl substituted compound has a much broader $S_c$ phase. Compared with examples 39 and 21 one can see that compound 11 has a preferred low melting point. A chain length of 8 C-atoms seems to be of advantage (see examples 1, 5 and 42).

EXAMPLE 12

4-(n-Butyldimethylsilyl)butyl
4-(5-octylpyrimdin-2-yl)phenyl ether

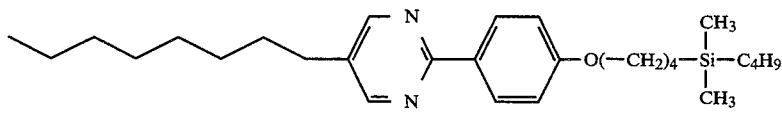

Phase sequence: K 16.7 $S_c$ 22.3 $S_A$ 25.9 I For a comparison with a non-invented substance we can use 5-octyl-2-(4-octyloxyphenyl)-pyrimidine, which exhibits the following phase sequence: K 29 $S_c$ 55 $S_A$ 62 N 69 I. The compound exhibits a lower melting point than this unsubstituted phenyl pyrimidine. For a comparison of the position of the dimethylsilane group in the alkyl chain we can take examples 48 and 24. Both examples have higher melting points so the point of example 12 is preferred.

EXAMPLE 13

4-(n-Butyldimethylsilyl)butyl
4-(4-decyloxybenzoyloxy)-phenyl ether

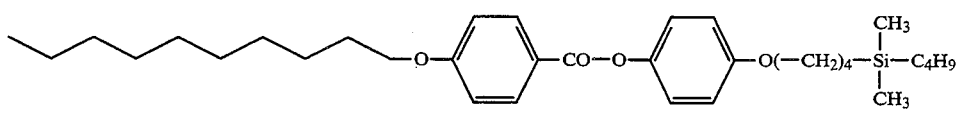

Phase sequence: K 18.7 $S_3$ (6.5) $S_c$ 43.8 $S_A$ 47.2 I For a comparison with a non-invented substance one can use 4-decyloxy-4-nonyloxyphenylbenzoat, which has the following phase sequence: K 75 $S_c$ 87 $S_A$ 89 N 91 I. The inventive compound has a very low melting point. Compared with the example 26 one can see that the position of the dimethylsilyl group is important for a low melting point.

EXAMPLE 14

4-(n-Butyldimethylsilyl)butyl
2-(4-octyloxyphenyl)-pyrimidin-5-yl ether

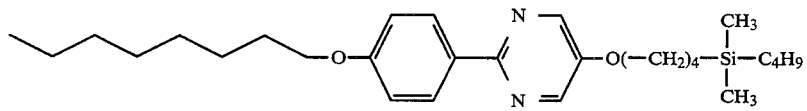

Phase sequence: K 36.4 $S_A$ (30.6) N (30.7) I

EXAMPLE 15

6-(Trimethylsilyl)hexyl
4-(2-octyloxypyrimidin-5-yl)-phenyl ether

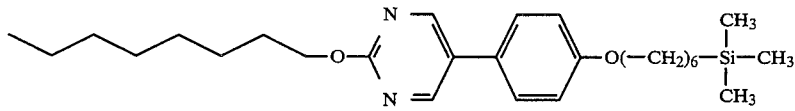

Phase sequence: K 68.1 $S_c$ 70.6 I

EXAMPLE 16

6-(Trimethylsilyl)hexyl
4-(2-octylpyrimidin-5-yl)phenyl ether

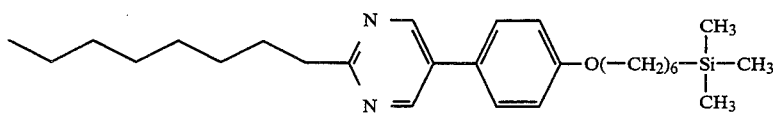

EXAMPLE 17

6-(Trimethylsilyl)hexyl
4-(5-octylpyrimidin-2-yl)phenyl ether

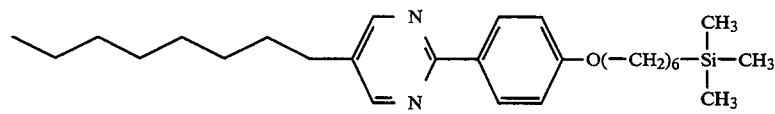

Phase sequence: K 25 $S_c$ 47 $S_A$ 56.6 I

In comparison to the following unsubstituted compound 5-octyl-2-(4-octyloxy-phenyl)-pyrimidine, which has the following phase sequence: K 29 $S_c$ 55 $S_A$ 62 N 69 I, The inventive compound has a melting point which is 4 degrees lower. Comparing the inventive compound with the examples 4, 37, 49 and 52 it can be seen that the shortening of the spacer is the reason for a melting point increase and that a length of the carbon chain of 7 carbon atoms is advantageous.

EXAMPLE 18

6-(Trimethylsilyl)hexyl
2-(4-octyloxyphenyl)pyrimidin-5-yl ether

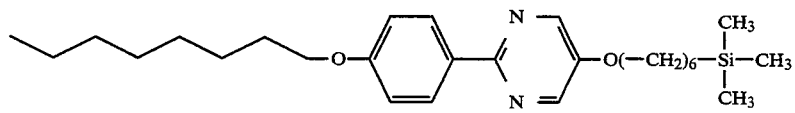

Phase sequence: K 38.7 $S_c$ 64.5 I

EXAMPLE 19

6-(Trimethylsilyl)hexyl
4-(2-octylthiopyrimidin-5-yl)-phenyl ether

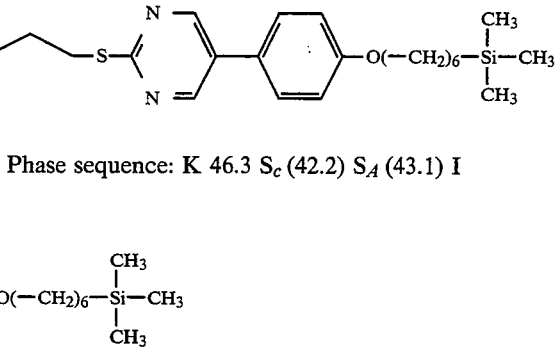

Phase sequence: K 46.3 $S_c$ (42.2) $S_A$ (43.1) I

EXAMPLE 20

6-(Trimethylsilyl)hexyl 4-(5-octylpyridin-2-yl)phenyl ether

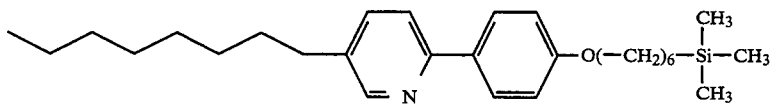

Phase sequence: K 28.3 $S_2$ 37.8 $S_c$ 60.2 I

EXAMPLE 21

6-(Ethyldimethylsilyl)hexyl
4-(5-octyloxypyrimidin-2-yl)phenyl ether

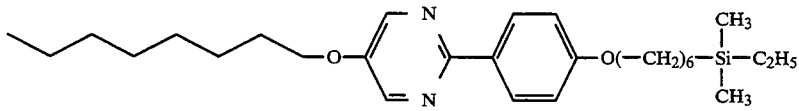

Phase sequence: K 38.6 $S_c$ 78 $S_A$ 84 I

EXAMPLE 22

6-(Ethyldimethylsilyl)hexyl
4-(2-octyloxypyrimidin-5-yl)phenyl ether

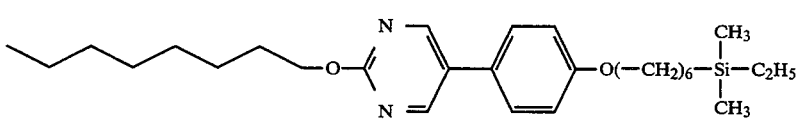

Phase sequence: K 58.6 $S_c$ 62.5 I

EXAMPLE 23

6-(Ethyldimethylsilyl)hexyl
4-(2-octylpyrimidin-5-yl)-phenyl ether

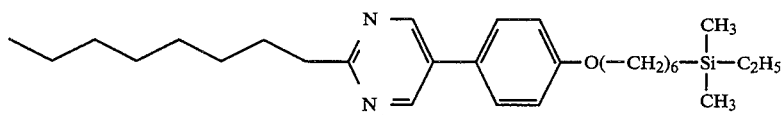

Phase sequence: K 39.8 $S_c$ 42.7 $S_A$ 47.6 I

EXAMPLE 24

6-(Ethyldimethylsilyl)hexyl
4-(5-octylpyrimidin-2-yl)-phenyl ether

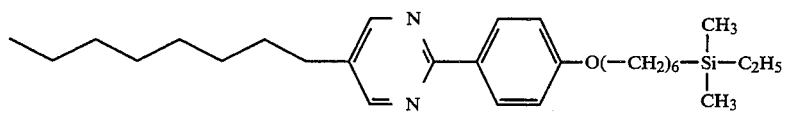

Phase sequence: K 22.6 $S_c$ 41.6 $S_A$ 50.4 I

The inventive compound has a melting point which is 6° C. lower than the melting point of an unsubstituted 5-octyl-2-(4-octyloxyphenyl)-pyrimidine, which has the following phase sequence: K 29 $S_c$ 55 $S_A$ 62 N 69 I. Comparing the inventive compound with the examples 8, 33, 50 and 53, one can see that the increasing and the shortening of the spacer leads to a melting point increase and that a chain length of 8 carbon atoms is the optimum.

EXAMPLE 25

6-(Ethyldimethylsilyl)hexyl
2-(4-octyloxyphenyl)-pyrimidin-5-yl ether

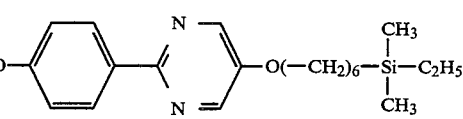

Phase sequence: K 28.7 $S_c$ 56 I

EXAMPLE 26

6-(Ethyldimethylsilyl)hexyl
4-(4-decyloxybenzoyloxy)-phenyl ether

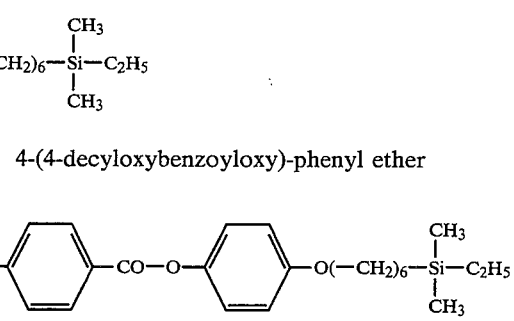

Phase sequence: K 55.2 $S_x$ (34.6) $S_c$ 67.4 $S_A$ 68.5 I

EXAMPLE 27

11-(Trimethylsilyl)undecyl
4-(4-octyloxybenzoyloxy)phenyl ether

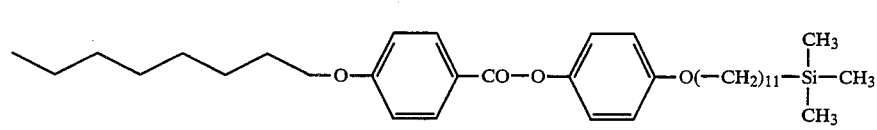

Phase sequence: K 53.5 $S_c$ 78.3 $S_A$ 81.2 I

EXAMPLE 28

11-(Trimethylsilyl)undecyl
4-(2-octylthiopyrimidin-5-yl)phenyl ether

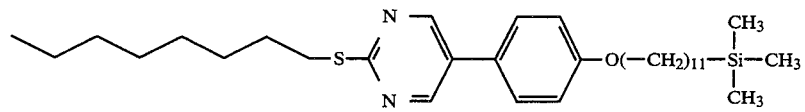

Phase sequence: K 68.5 $S_2$ (47.2) $S_c$ 68.6 I

EXAMPLE 29

11-(Trimethylsilyl)undecyl
2-(4-octyloxyphenyl)pyrimidin-5-yl ether

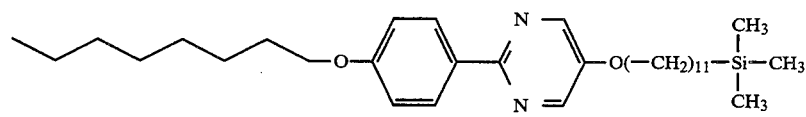

Phase sequence: K 69.4 S$_c$ 92.0 I

EXAMPLE 30

11-(Trimethylsilyl)undecyl
4-(5-octylpyridin-2-yl)phenyl ether

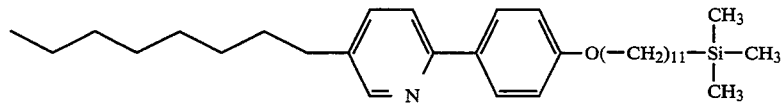

Phase sequence: K 48.3 S$_2$ 60 S$_c$ 76.1 I

EXAMPLE 31

11-(Trimethylsilyl)undecyl
2-(4-dodecyloxyphenyl)-pyrimidin-5-yl ether

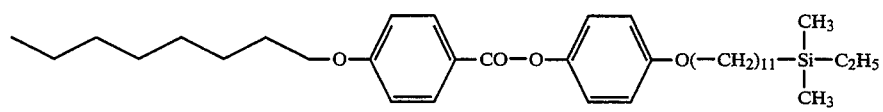

Phase sequence: K 81.6 S$_c$ 89.9 I

EXAMPLE 32

11-(Ethyldimethylsilyl)undecyl
4-(2-octylthiopyrimidin-5-yl)phenyl ether

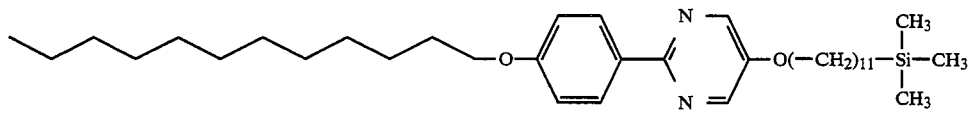

Phase sequence: K 64 S$_2$ [40] S$_c$ [63] I

EXAMPLE 33

11-(Ethyldimethylsilyl)undecyl
4-(5-octylpyrimidin-2-yl)phenyl ether

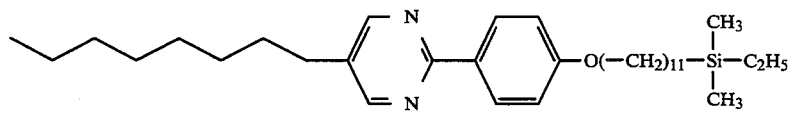

Phase sequence: K 45.7 S$_c$ 58.6 S$_A$ 58.9 I

EXAMPLE 34

11-(Ethyldimethylsilyl)undecyl
4-(4-octyloxybenzoyloxy)-phenyl ether

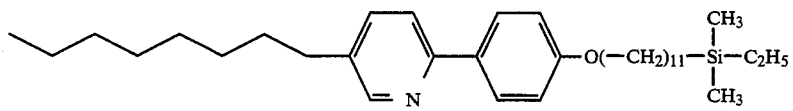

Phase sequence: K 57 S$_c$ 74.8 S$_A$ 77.5 I

EXAMPLE 35

11-(Ethyldimethylsilyl)undecyl
4-(5-octylpyridin-2-yl)phenyl ether

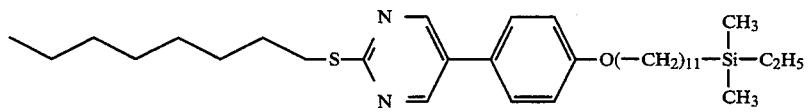

Phase sequence: K 41 S$_2$ 57 S$_c$ 71 I

EXAMPLE 36

11-(Ethyldimethylsilyl)undecyl
2-(4-dodecyloxyphenyl)-pyrimidin-5-yl ether

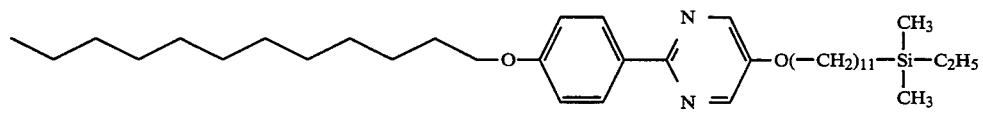

Phase sequence: K 75.4 S$_c$ 84.9 I

EXAMPLE 37

11-(Trimethylsilyl)undecyl 4-(5-octylpyrimidin-2-yl)phenyl ether

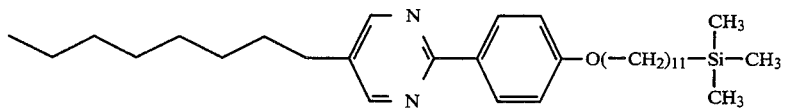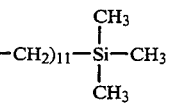

2 g (4.6 mmol) of 10-undecenyl 4-(5-octylpyrimidin-2-yl)phenyl ether, 6 g (63.4 mmol) of chlorodimethylsilane and 0.1 ml of a 0.1 molar solution of $H_2PtCl_6$ in isopropanol are heated at 100° C. for 8 h in a sealed glass tube. After opening the tube, the product is evaporated down, taken up in 10 ml of dry tetrahydrofuran and mixed with 50 ml of a 1 molar solution of methylmagnesium bromide in tetrahydrofuran. After heating for 2 hours under reflux, the mixture is hydrolyzed in a saturated aqueous $NH_4Cl$ solution and the aqueous solution is extracted repeatedly with diethyl ether. The combined organic phases are washed with saturated NaCl solution, dried over $MgSO_4$ and evaporated down in vacuo. After chromatographic purification ($SiO_2$, $CH_2Cl_2$/hexane 3/1) and recrystallization from methanol, 700 mg of colorless crystals are obtained.

Phase sequence: K 56.7 $S_c$ 63.8 I

EXAMPLE 38

3-(Butyldimethylsilyl)propyl 4-(5-octyloxypyrimidin-2-yl)phenyl ether

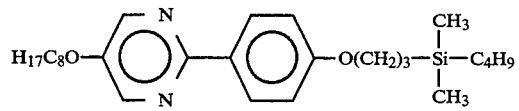

1.42 g (5 mmol) of 2-(4-hydroxyphenyl)-5-octyloxypyrimidine in 10 ml of DMF and 3-butyldimethylsilyl-1-bromopropane in 5 ml of DMF are added dropwise to 0.3 g (10 mmol) of 80% sodium hydride in 2 ml of dimethylformamide (DMF) and stirred for 2 hours up to 60° C. After hydrolysis with 0.5 ml of methanol, the reaction solution is taken up in 40 ml of ice-cold water, adjusted to a pH of 6–7 with 1 N HCl and extracted with dichloromethane. The organic phase is washed with common salt solution, dried over magnesium sulfate and evaporated down in vacuo. After chromatographing purification ($SiO_2$, hexane/dichloromethane 1:1) and recrystallization from isopropanol, 1.28 g of colorless crystals are obtained.

$K_2$ 34(23) K 50 $S_c$ 65 $S_A$ 68 I

The following were obtained analogously:

EXAMPLE 39

3-(Pentyldimethylsilyl)propyl 4-(5-octyloxypyrimidin-2-yl)phenyl ether

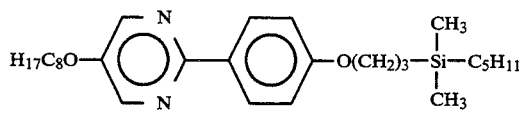

$K_2$ 36(16) K 55 $S_c$ 60 $S_A$ 64 I

EXAMPLE 40

5-(Trimethylsilyl)pentyl 4-(5-octyloxypyrimidin-2-yl)-phenyl ether

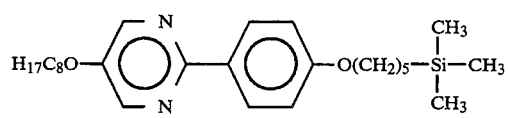

K 68.6 $S_c$ 88.2 $S_A$ 93.3 I

EXAMPLE 41

5-(Ethyldimethylsilyl)pentyl 4-(5-octyloxypyrimidin-2-yl)phenyl ether

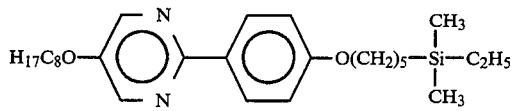

K 66.1 $S_c$ 83 $S_A$ 87.2 I

EXAMPLE 42

5-(Butyldimethylsilyl)pentyl 4-(5-octyloxypyrimidin-2-yl)phenyl ether

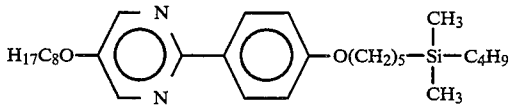

$K_2$ 25.3 $K_1$ 37.7 $S_c$ 75 $S_A$ 81 I

EXAMPLE 43

6-(Trimethylsilyl)hexyl 4-(5-octyloxypyrimidin-2-yl)-phenyl ether

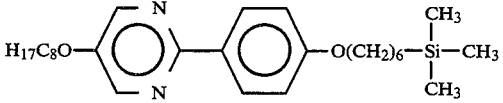

EXAMPLE 44

6-(Ethyldimethylsilyl)hexyl 4-(5-heptyloxypyrimidin-2-yl)phenyl ether

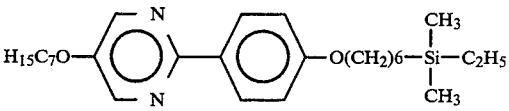

$K_2$ [21.6] K 36.2 $S_c$ 71 $S_A$ 81 I

EXAMPLE 45

10-(Trimethylsilyl)decyl
4-(5-octyloxypyrimidin-2-yl)-phenyl ether

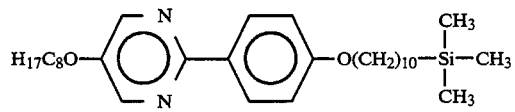

$K_2$ 18.9 $K_1$ 40 $S_c$ 84 $S_A$ 92 I

EXAMPLE 46

10-(Ethyldimethylsilyl)decyl
4-(5-octyloxypyrimidin-2-yl)phenyl ether

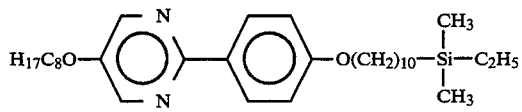

K 13.1 $S_c$ 79 $S_A$ 88 I

EXAMPLE 47

3-(Butyldimethylsilyl)propyl
4-(5-octylpyrimidin-2-yl)-phenyl ether

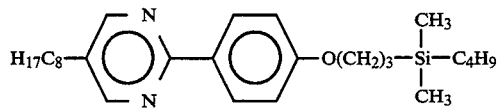

K 31.4 $S_A$ 39.2 I

EXAMPLE 48

3-(Pentyldimethylsilyl)propyl
4-(5-octylpyrimidin-2-yl)phenyl ether

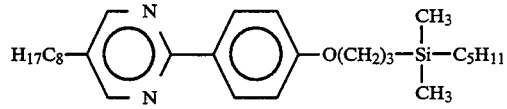

[$K_2$ 27.9] $K_1$ 32.2 [$S_c$ 11] $S_A$ 34.5 I

EXAMPLE 49

5-(Trimethylsilyl)pentyl
4-(5-octylpyrimidin-2-yl)phenyl ether

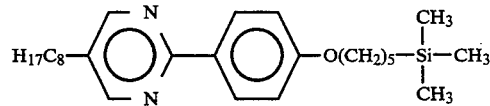

K 50.6 [$S_c$ 42] $S_A$ 60 I

EXAMPLE 50

5-(Ethyldimethylsilyl)pentyl
4-(5-octylpyrimidin-2-yl)phenyl ether

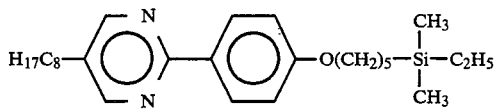

K 48.4 $S_A$ 54 I

EXAMPLE 51

5-(Butyldimethylsilyl)pentyl
4-(5-octylpyrimidin-2-yl)phenyl ether

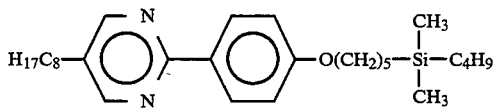

$K_2$ 16.2 $S_A$ 47.5 I

EXAMPLE 52

10-(Trimethylsilyl)decyl
4-(5-octylpyrimidin-2-yl)phenyl ether

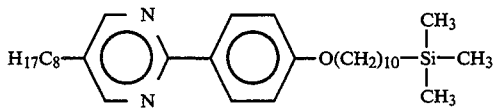

K 50.1 $S_c$ 60.7 $S_A$ 61 I

EXAMPLE 53

10-(Ethyldimethylsilyl)decyl
4-(5-octylpyrimidin-2-yl)phenyl ether

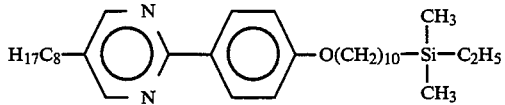

K 42.6 $S_c$ 56.4 $S_A$ 56.5 I

EXAMPLE 54

6-(Trimethylsilyl)hexyl
4-(5-dodecylpyrimidin-2-yl)phenyl ether

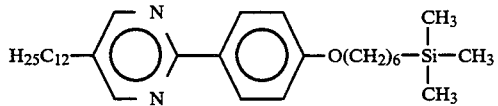

[$K_2$ 32.2] K 46.3 [$S_2$ 12] $S_c$ 60 I

EXAMPLE 55

4-(Cyclohexyldimethylsilyl)butyl 4-(5-octylpyrimidin-2-yl)phenyl ether

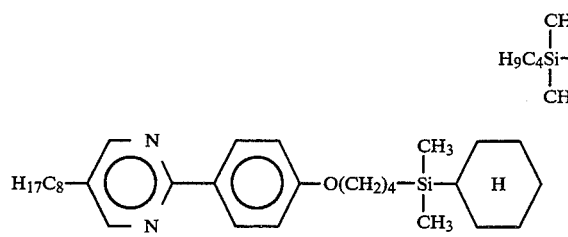

X 45 $S_c$ (10) $S_A$ (17) I

EXAMPLE 56

6-(Ethyldimethylsilyl)hexyl 2-(4-[4-butyloxy]butyloxyphenyl)pyrimidin-5-yl ether

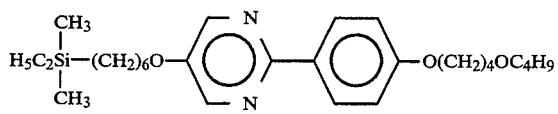

K 42.2 [$S_c$ 41.8] I

EXAMPLE 57

4-(5-[4-Butyldimethylsilyl]butoxypyrimidin-2-yl)phenyl 4-trans-pentylcyclohexanecarboxylate

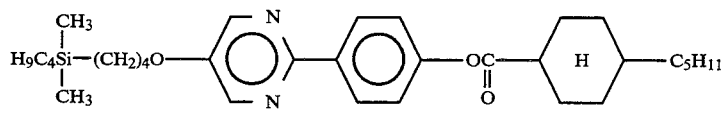

K 82 $S_A$ 80N 123.5 I

EXAMPLE 58

4-(Butyldimethylsilyl)butyl 2-(6-cyclopropylhexyloxyphenyl)pyrimidin-5-yl ether

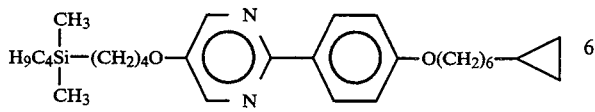

M.p. 42–43

EXAMPLE 59

4-(Butyldimethylsilyl)butyl 2-(4-[4-nonyloxybenzyloxy]-phenyl)pyrimidin-5-yl ether

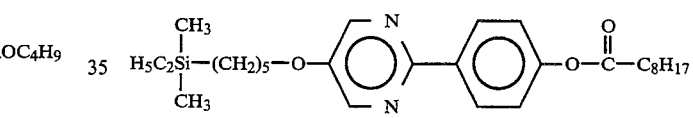

X 62 $S_c$ 98 I

EXAMPLE 60

4-(5-[4-Butyldimethylsilylbutyloxy]pyrimidin-2-yl)phenyl (2R, 3R)-3-propyloxirane-2-carboxylate

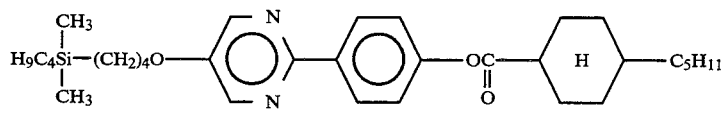

$(\alpha)_D = -9.08°$ (c=2, CHCl$_3$)

EXAMPLE 61

4-(5-]5-Ethyldimethylsilylpentyloxy]pyrimidin-2-yl)phenyl nonanoate

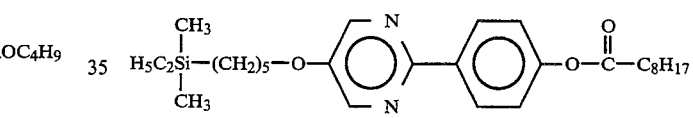

X 65 I

EXAMPLE 62

(2S, 3S)-3-Butyloxirane-2-methyl 4-(5-[4-butyldimethylsilylbutyloxy]pyrimidin-2-yl)phenyl ether

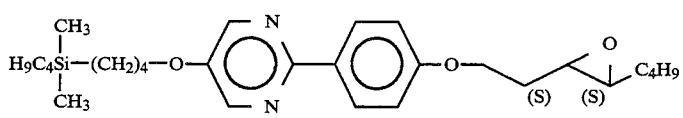

X 79 I $(\alpha) = -13.2°$ (c=2, CHCl$_3$)

EXAMPLE 63

(2S, 3S)-3-Butyloxirane-2-methyl
2-(4-[4-butyldimethylsilylbutyloxy]phenyl)pyrimidin-5-yl ether

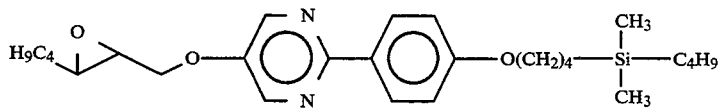

X 50 S$_c$ 80.5 S$_A$ 87 I (α)= −15.6° (c=2, CHCl$_3$)

EXAMPLE 64

4-(5-Octylpyrimidin-2-yl)phenyl
2,3-difluoro-4-(3-butyldimethylsilylpropyloxy)benzoate

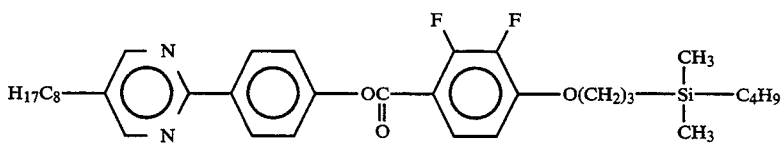

X 59 S$_c$ 99 I

EXAMPLE 65

4-(2-Octyloxypyrimidin-5-yl)phenyl
2,3-difluoro-4-(3-butyldimethylsilylpropyloxy)benzoate

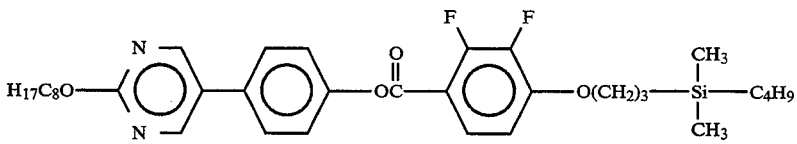

X 66 S$_c$ 128 I

EXAMPLE 66 4-(5-Octyloxypyrimidin-2-yl)phenyl
2,3-difluoro-4-(3-butyldimethylsilylpropyloxy)benzoate

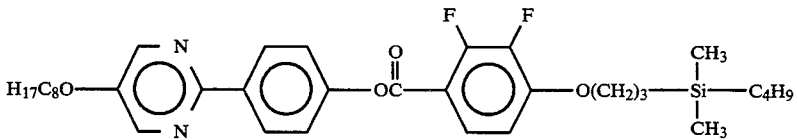

X 67 S$_x$ 111 S$_c$ 125 I

EXAMPLE 67

4-(Butyldimethylsilyl)butyl
4-(2-nonyloxypyrimidin-5-yl)phenyl ether

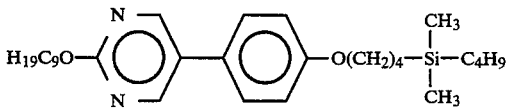

X 33 S$_c$ (27) I

EXAMPLE 68

4-(Butyldimethylsilyl)butyl
4-(2-decyloxypyrimidin-5-yl)phenyl ether

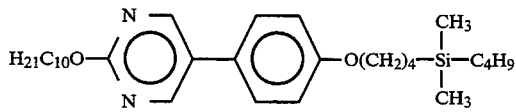

X 40.2 S$_c$ (30) I

EXAMPLE 69

4-(Cyclohexyldimethylsilyl)butyl
4-(2-octyloxypyrimidin-5-yl)phenyl ether

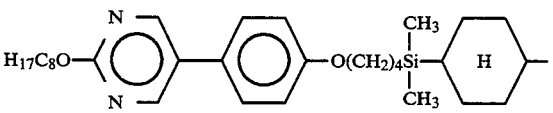

X 52 I

EXAMPLE 70

4-(Butyldimethylsilyl)butyl
4-(2-hexyloxypyrimidin-5-yl)phenyl ether

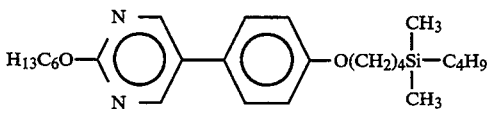

X 47 I

EXAMPLE 71

4-(Butyldimethylsilyl)butyl
4-(2-heptyloxypyrimidin-5-yl)phenyl ether

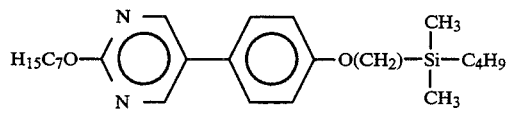

X 44.6 I

EXAMPLE 72

4-(Butyldimethylsilyl)butyl
4-(2-perfluoroheptylmethyloxypyrimidin-5-yl)phenyl ether

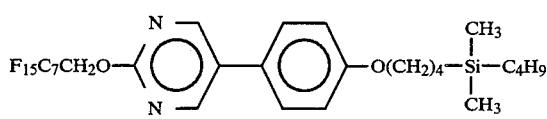

X 37 S$_C$ (18) S$_A$ 35 I

EXAMPLE 73

4-(Butyldimethylsilyl)butyl
4-(2-[11-undecenyloxy]-pyrimidin-5-yl)phenyl ether

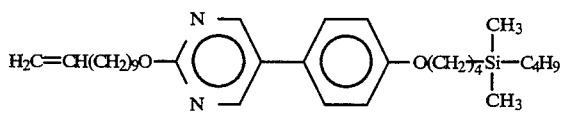

X 38 I

EXAMPLE 74

4-(Butyldimethylsilyl)butyl
4-(5-[4-hexyloxyphenyl]-pyrimidin-2-yl)phenyl ether

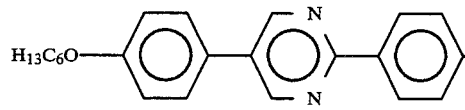

X 57 S$_G$ 53 S$_F$ 88 S$_c$ 157 S$_A$ 172 I

EXAMPLE 75

4-(Butyldimethylsilyl)butyl
4-(5-[4-decylphenyl]-1,3,4-thiadiazol-2-yl)phenyl ether

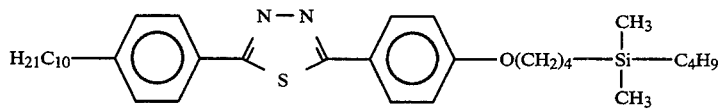

X 44 S$_C$ 116 I

EXAMPLE 76

Pyrimidin-2-ylphenyl
4,5-bis[4-(butyldimethylsilyl)butyl]ether

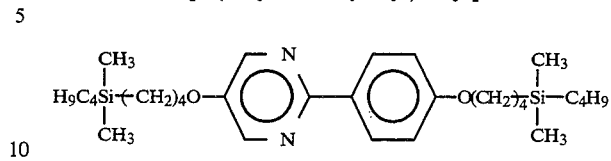

X 24 I

EXAMPLE 77

4-(5-[4-Butyldimethylsilyl]butoxypyrimidin-2-yl)phenyl (2R)-tetrahydrofuran-2-carboxylate

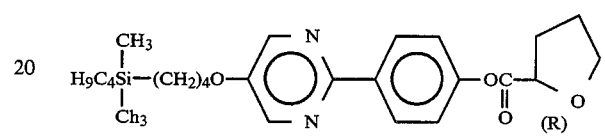

(α) = −7.65° (c=2, CHCl$_3$)

EXAMPLE 78

4'-(5''-Butyldimethylsilylbutyloxypyrimidin-2''-yl)phenyl 4-octyloxybenzoate

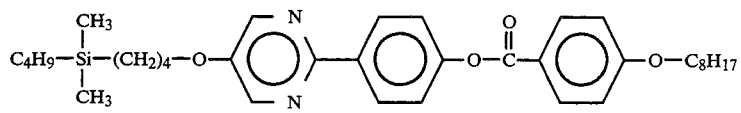

X 43 S$_c$ 89 N 126 I

EXAMPLE 79

(2R)-[2(4-Butyldimethylsilyl-butyloxyphenyl)pyrimidine-5-yl]-lactic acid-ethylester

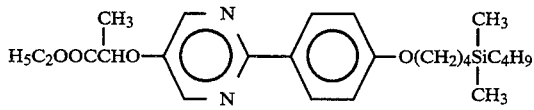

Fp = 57.6° C[α]$_D$= +36.6°

APPLICATION EXAMPLE 1

A binary mixture of an alkyl and a silyl compound 5-octyloxy-2-(4-pentyloxyphenyl)pyrimidin (56 mol%) and 4-(ethyldimethylsilyl)butyl 4-(5-octyloxypyrimidin-2-yl)phenyl ether (44 mol%) has the following phase sequence:

K 16 $S_c$ 76.8 $S_A$ 84.4 I.

This mixture has a lower melting point than the analogous alkyl mixture 5-octyloxy-2-(4-pentyloxyphenyl)pyrimidine (52 mol%) and 5-octyloxy-2-(4-octyloxyphenyl)pyrimidin (48 mol%)

K 25 $S_c$ 85 $S_A$ 95 N 97 I

APPLICATION EXAMPLE 2

A binary mixture of two silyl compounds (equal mol%)

4-(butyldimethylsilyl)butyl 4-(4-decyloxybenzoyloxy)-phenyl ether and 6-(trimethylsilyl)hexyl 2-(4-octyloxyphenyl)pyrimidin-5-yl ether has the following phase sequence:

K 9 $S_c$ 47 $S_A$ 50 I.

APPLICATION EXAMPLE 3

The binary mixture of two silyl compounds 6-(ethyldimethylsilyl)hexyl 2-(4-octyloxyphenyl)-pyrimidin-5-yl ether (45 mol%) and 4-(ethyldimethylsilyl)butyl 4-(5-octylpyrimidin-2-yl)-phenyl ether (55 mol%) has the phase sequence:

K 12.5 $S_c$ 63 I.

APPLICATION EXAMPLE 4

A mixture of 6-(ethyldimethylsilyl)hexyl 4-(5-octyloxypyrimidin-2-yl)phenyl ether (47 mol%), 4-(5-dodecyloxypyrimidin-2-yl)phenyl trans-4-pentylcyclohexanecarboxylate (18 mol%), 4-(5-octyloxypyrimidin-2-yl)phenyl trans-4-pentylcyclohexanecarboxylate (22 mol%), and 5-octyloxy-2-(4-ethyloxyphenyl)pyrimidine (13 mol%) has the phase sequence: K 17 $S_c$ 91 $S_A$ 101 N 115 I.

APPLICATION EXAMPLE 5

A ferroelectric multicomponent mixture which contains 7.5 mol % of 4-(ethyldimethylsilyl)butyl 4-(5-octyloxypyrimidin-2-yl)phenyl ether and 17.5 mol % of 4-(butyldimethylsilyl)butyl 4-(5-octyloxypyrimidin-2-yl)phenyl ether in "Felix-001"*) (75 mol %), has the following phase sequence:

K −5 $S_c$* 71 $S_A$* 84 N* 88 I

The mixture can be satisfactorily oriented by conventional methods.

Despite lower spontaneous polarization ($P_s$=4.5 nC/cm$^2$), this mixture exhibits, for example at 25° C., a shorter switching time ($\tau_{0-90}$=135 μs) ($\tau_{10-90}$=75 μs), a lower viscosity, a higher effective tilt angle ($2\theta_{eff}$=19°) than "Felix 001" and consequently, a very good contrast.

*) —C. Escher, H.—R. Dübal, W. Hemmerling, I. Müller, D. Ohlendorf and R. Wingen, presented at 1st International Symposium on Ferroelectric Liquid Crystals, Arcachon-Bordeaux, France, Sep. 21–23, 1987, commercial mixture supplied by Hoechst Aktiengesellschaft—

APPLICATION EXAMPLE 6

The compound 4-(Butyldimethylsilyl)butyl 4-(5-octyloxypyrimidin-2-yl)phenyl ether has the phase sequence:

K 16.5 $S_c$ 63.1 $S_A$ 64 I and consequently has a substantially lower melting point and consequently a wider $S_c$ phase range than 5-octyloxy-2-(4-decyloxyphenyl)-pyrimidine having the phase sequence K 50 $S_c$ 89 $S_A$ 99.

APPLICATION EXAMPLE 7 a) A mixture composed of the 6 components

| | |
|---|---|
| 5-octyloxy-2-(4-hexyloxyphenyl)pyrimidine | 16.7 mol % |
| 5-octyloxy-2-(4-octyloxyphenyl)pyrimidine | 7.7 mol % |
| 5-octyloxy-2-(4-butyloxyphenyl)pyrimidine | 17.6 mol % |
| 5-octyloxy-2-(4-decyloxyphenyl)pyrimidine | 14 mol % |
| 5-octyl-2-(4-[9-cyclopropylnonyloxy]phenyl)-pyrimidine | 24 mol % |
| 5-octyloxy-2-(4-[butyldimethylsilylbutyloxy]-phenyl)pyrimidine | 20 mol % | exhibits the following liquid crystalline phase ranges:

X 2.6 $S_c$ 59 $S_A$ 82 I.

b) In comparison therewith, the liquid-crystalline mixture which differs from the abovementioned mixture only in that it contains no silyl component has the following phase ranges:

X 5.1 $S_c$ 68 $S_A$ 83 N 85 I

The addition of the silyl component therefore results apparently in a lowering of the melting point by 2.5° C.

c) For a comparison, also the following mixture which differs from the mixture 7a only in that it contains, instead of the abovementioned silyl compound, 20 mol % of

| | |
|---|---|
| 5-octyloxy-2-(4-[ethyldimethylsilylbutyloxy]phenyl)-pyrimidine | 20 mol % | is presented and has the following liquid-crystalline phase ranges:

X 7.4 $S_c$ 49.5 $S_A$ 87 I.

This example shows that the component selected in Example 7a is substantially more favorable, i.e. chain length and position of the dimethylsilyl group have a decisive effect. The butyldimethylsilyl component is apparently particularly favorable.

c) A further comparison mixture, which contains, in the mixture 7b, 25 mol % of 5-nonyloxypyrimidin-2-ylphenyl trans-4-pentylcyclohexanecarboxylate instead of the silyl compound, has the following phases:

X 27 $S_c$ 88 N 116 I.

Under the same conditions as in Example 7a, the sample crystallizes at a temperature of 10° C. The mixture 7a according to the invention has the advantage that the substance only crystallizes out at much lower temperatures.

APPLICATION EXAMPLE 8 a) A liquid-crystalline mixture composed of the following nine components

| | |
|---|---|
| 5-octyloxy-2-(4-hexyloxyphenyl)pyrimidine | 12 mol % |
| 5-octyloxy-2-(4-octyloxyphenyl)pyrimidine | 48 mol % |
| 5-octyloxy-2-(4-butyloxyphenyl)pyrimidine | 12 mol % |
| 5-octyloxy-2-(4-decyloxyphenyl)pyrimidine | 6.4 mol % |
| 5-octyloxy-2-(4-dodecyloxyphenyl)pyrimidine | 6.4 mol % |
| 5-octyl-2-(4-dodecyloxyphenyl)pyrimidine | 11.2 mol % |

-continued

| | |
|---|---|
| 4-(5-decylpyrimidin-2-yl)phenyl trans-4-pentylcyclohexanecarboxylate | 11.2 mol % |
| 4-(5-octylpyrimidin-2-yl)phenyl heptanoate | 16 mol % |
| 4-(butyldimethylsilylbutyloxy)phenyl 4-decyloxybenzoate | 20 mol % | has the following phase ranges:

$$X -5 S_c 60 S_A 76.5 N 83 I$$

The crystallization temperature at a cooling rate of 10° C. min$^{-1}$ is $-26°$ C.

b) To compare the physical properties, the phase ranges of a mixture were measured which differs from the above-mentioned one only in that it contains no silyl component. This comparison mixture has the following phase ranges $$X -3.5 S_c 69 S_A 80 N 92 I$$

The crystallization temperature under the abovementioned cooling conditions is $-19°$ C. The silyl component apparently leads to a lowering of the melting point and of the crystallization temperature.

APPLICATION EXAMPLE 9 a) A ferroelectric mixture composed of
94 mol % of the mixture from Example 8a and
6 mol % of 5-(nonyloxypyrimidin-5-yl)phenyl (2S, 3S)-2-chloro-3-methylpentanoate
has the following phase ranges:

$$X -14 S_c* 61 S_A* 74 N* 80 I$$

At a temperature of 25° C., this mixture has a polarization of $-5.7$ nC/cm$^2$ and switches at $\tau=116.1$ μs for a voltage of 10 V/μm. The effective tilt angle of this mixture is 8.4°.

b) A comparison mixture containing 94 mol % of the mixture from Example 8b has the following phase ranges:

$$X-6S_c71S_A77N89I$$

At a temperature of 25° C., this mixture has a polarization of $-9$ nC/cm$^2$ and switches at $\tau=43$ μs for a voltage of 10 V/μm. The effective tilt angle of this mixture is 7.2°.

The comparison of Examples 9a and 9b reveals that the silyl component in ferroelectric mixtures lowers the melting point, and increases the effective angle and consequently, the transmission in the clear state.

c) In order to assess the effect of the silyl component on the switching time, a mixture is required which contains the same components as the mixture in Example 9b, but contains precisely 4% of the dopant instead of 6%. At a temperature of 25° C., this mixture has a polarization of $-5.8$ nC/cm$^2$ and switches at a field of 10 V/μm with a switching time of 180 μs. Since the spontaneous polarization of this mixture is just as large as in the mixture 9a, the two switching times of these ferroelectric mixtures are comparable and it is evident that the mixture containing the component according to the invention switches markedly faster.

APPLICATION EXAMPLE 10 a) A mixture composed of the 4 components

| | |
|---|---|
| 5-octyloxy-2-(4-hexyloxyphenyl)pyrimidine | 30 mol % |
| 5-octyloxy-2-(4-octyloxyphenyl)pyrimidine | 20 mol % |
| 5-octyloxy-2-(4-butyloxyphenyl)pyrimidine | 25 mol % |
| 4-(5-[4-butyldimethylsilyl]butyloxypyrimidin-2-yl)phenyl trans-4-pentylcyclohexanecarboxylate | 25 mol % | has the following liquid-crystalline phase ranges:

$$X19S_c79S_AN102I$$

At a cooling rate of 10° C. min$^{-1}$, the substance crystallizes at a temperature of $-3°$ C.

b) Compared therewith, the liquid-crystalline mixture claimed in DE-3,831,226.3, which differs from the above-mentioned mixture only in that it does not contain a phenyl ester, has the following phase ranges:

$$X21.5S_c85S_A95N97.5I$$

Under the abovementioned conditions, the mixture crystallizes at 12° C. The silyl compound according to the invention results both in a lowering of the melting point and also in a drastic lowering of the crystallization temperature.

APPLICATION EXAMPLE 11 a) A liquid-crystalline mixture composed of the following components

| | |
|---|---|
| 5-octyloxy-2-(4-hexyloxyphenyl)pyrimidine | 12 mol % |
| 5-octyloxy-2-(4-octyloxyphenyl)pyrimidine | 4.8 mol % |
| 5-octyloxy-2-(4-butyloxyphenyl)pyrimidine | 12 mol % |
| 5-octyloxy-2-(4-decyloxyphenyl)pyrimidine | 6.4 mol % |
| 5-octyloxy-2-(4-dodecyloxyphenyl)pyrimidine | 6.4 mol % |
| 5-octyl-2-(4-dodecyloxyphenyl)pyrimidine | 11.2 mol % |
| 4-(5-decylpyrimidin-2-yl)phenyl trans-4-pentylcyclohexylcarboxylate | 11.2 mol % |
| 4-(5-octylpyrimidin-2-yl)phenyl heptanoate | 16 mol % |
| 2-(4-butyldimethylsilylbutyloxyphenyl)-5-(4-hexyloxyphenyl)pyrimidine | 20 mol % | has the following phase ranges:

$$X-3S_c82S_A110I.$$

In the experiment to produce a comparison mixture which contains 20 mol % of 2-(4'-octyloxyphenyl)-5-(4''-hexyloxyphenyl)pyrimidine instead of the silyl compound, it was possible to observe that this compound, in contrast to the abovementioned one, is not soluble at room temperature. The introduction of the dimethylsilyl group into the chain therefore results in an increase in the solubility of this compound in liquid-crystalline mixtures.

APPLICATION EXAMPLE 12 a) A mixture composed of the three components:

| | |
|---|---|
| 5-(4'-hexylphenyl)-2-(4'-octylphenyl)pyrimidine | 36.6 mol % |
| 5-(4'-pentyloxyphenyl)-2-(4''-hexylphenyl)pyrimidine | 23.4 mol % |
| 5-(4'-hexyloxyphenyl)-2-(4''-butyldimethylsilylbutyloxyphenyl)pyrimidine | 40 mol % | has the following phase ranges:

$$X 27 S_F 43 S_c 95 S_A 192 I$$

b) Compared therewith, the following binary mixture, which differs only in that it contains no silyl component, has the following phase ranges:

X 58 S$_F$ 100 S$_C$ 131 S$_A$ 198 I

The addition of the component according to the invention apparently leads to a substantial lowering of the melting point.

APPLICATION EXAMPLE 13 a) A mixture composed of the following four substances

| | |
|---|---|
| 5-octyloxy-2-(4'-butyloxyphenyl)pyrimidine | 39.6 mol % |
| 5-cyclopropyl-2-(4'-butyloxyphenyl)pyrimidine | 32.4 mol % |
| 4-(5-decyloxypyrimidin-2-yl)phenyl trans-4-pentylcyclohexylcarboxylate | 18 mol % |
| 5-octyloxy-2-(butyldimethylsilylbutyloxyphenyl)pyrimidine | 10 mol % | has the following phase ranges:

X 15 S$_C$ 79 S$_A$ 85 N 98 I b) Compared therewith, the mixture which differs only in that it contains no silyl component has the following phase ranges:

X 20 S$_C$ 79.5 S$_A$ 87 N 108 I

The addition of the silyl component apparently results in a lowering of the melting point.

APPLICATION EXAMPLE 14

A mixture composed of 80 mol % of the mixture of Example 13a and 20 mol % of 4-decyloxy-(4'-butyldimethylsilylbutyloxyphenyl) benzoate has the following phases:

X 0 S$_C$ 65 S$_A$ 78 N 91 I

The comparison with the mixture of Example 13a shows that this silyl component has lowered the melting point by 15° C.

APPLICATION EXAMPLE 15 a) A ferroelectric mixture is composed of
92.66 mol % of the mixture of Example 14
4.02 mol % of 4-(2-octyloxypyrimidin-5-yl)phenyl 2R, 3R-3-propyloxirane-2-carboxylate
3.32 mol % of (S)-4-(2-octyloxypyrimidin-5-yl)phenyl [spiro(1,3-dioxylane-2,1'-cyclohexane)-4-yl]methyl ether
and has the following phase sequence:

X S$_C$ 65 S$_A$ 77 N 85 I.

At 25° C., the mixture has a polarization of 17 nC cm$^{-2}$ and switches with a switching time $\tau$=102 μs at a field of 10 V/μm.

APPLICATION EXAMPLE 16

A binary mixture composed of the two components

| | |
|---|---|
| 2-(butyldimethylsilylbutyloxyphenyl)-5-octyloxypyrimidine | 68 mol % |
| 2-(butyloxybutyloxyphenyl)-5-(ethyldimethylsilyloxy)-pyrimidine | 32 mol % | has the following phase ranges:

X O S$_C$ 55 I.

This example proves that silylphenylpyrimidines are suitable in a quite special way for preparing liquid-crystalline mixtures with low melting points.

APPLICATION EXAMPLE 17 a) A mixture of the following components

| | |
|---|---|
| 4-(5-dodecyloxypyrimidin-2-yl)phenyl trans-4-pentylcyclohexanecarboxylate | 28 mol % |
| 4-(5-octyloxypyrimidin-2-yl)phenyl trans-4-pentylcyclohexanecarboxylate | 42 mol % |
| 4-(4-butyldimethylsilyl)butyloxyphenyl 4-decyloxybenzoate | 30 mol % | has the following phase ranges:

X 16 S$_C$ 64.5 S$_A$ 81 N 92 I b) A comparison mixture which differs from the mixture 17a in that it contains no silyl component, has the following phase ranges:

X 42 S$_2$ 58 S$_C$ 116 N 186 I.

The addition of the silyl compound results, however, in a lowering of the melting point by 26° C.

APPLICATION EXAMPLE 18 a) A mixture composed of the components

| | |
|---|---|
| 5-octyloxy-2-(4-hexyloxyphenyl)pyrimidine | 23.8 mol % |
| 5-octyloxy-2-(4-octyloxyphenyl)pyrimidine | 11 mol % |
| 5-octyloxy-2-(4-butyloxyphenyl)pyrimidine | 25.2 mol % |
| 5-octyloxy-2-(4-decyloxyphenyl)pyrimidine | 20 mol % |
| 4'-(ethyldimethylsilylhexyloxy)phenyl 4-decyloxybenzoate | 20 mol % | has the following liquid-crystalline phase ranges:

X 9 S$_C$ 54 S$_A$ 88 I.

b) Compared therewith, the liquid-crystalline mixture claimed in DE 3,831,226.3, which differs from the above-mentioned mixture only in that it contains no silyl compound, has the following phase ranges:

X 13 S$_C$ 81 S$_A$ 95 N 98 I.

The addition of the silyl compound results in a lowering of the melting point.

APPLICATION EXAMPLE 19 a) A mixture composed of the components

| | |
|---|---|
| 5-octyloxy-2-(4-hexyloxyphenyl)pyrimidine | 23.8 mol % |
| 5-octyloxy-2-(4-octyloxyphenyl)pyrimidine | 11 mol % |
| 5-octyloxy-2-(4-butyloxyphenyl)pyrimidine | 25.2 mol % |
| 5-octyloxy-2-(4-decyloxyphenyl)pyrimidine | 20 mol % |
| 4'-(butyldimethylsilylbutyloxy)phenyl 4- | 20 mol % |

-continued decyloxybenzoate has the following liquid-crystalline phase ranges:

X 10 S$_c$ 40 S$_A$ 85 I.

b) Compared therewith, the liquid-crystalline mixture claimed in DE 3,831,226.3, which differs from the above-mentioned mixture only in that it contains no silyl compound, has the following phase ranges:

X 13 S$_c$ 81 S$_A$ 95 N 98 I.

The addition of the silyl compound therefore results in a lowering of the melting point.

APPLICATION EXAMPLE 20 a) A mixture composed of the components

| | |
|---|---|
| 5-octyloxy-2-(4-hexyloxyphenyl)pyrimidine | 23.8 mol % |
| 5-octyloxy-2-(4-octyloxyphenyl)pyrimidine | 11 mol % |
| 5-octyloxy-2-(4-butyloxyphenyl)pyrimidine | 25.2 mol % |
| 5-octyloxy-2-(4-decyloxyphenyl)pyrimidine | 20 mol % |
| 5-octyl-2-[4-(cyclohexyldimethylsilylbutyloxy) phenyl]-pyrimidine | 20 mol % | has the following liquid-crystalline phase ranges:

X 8 S$_c$ 59 S$_A$ 83 I.

b) Compared therewith, the liquid-crystalline mixture claimed in DE 3,831,226.3, which differs from the above-mentioned mixture only in that it contains no silyl compound, has the following phase ranges:

X 13 S$_c$ 81 S$_A$ 85 N 98 I.

The addition of this silyl compound results in a lowering of the melting point of 5° C.

APPLICATION EXAMPLE 21

A mixture composed of 80 mol % of the mixture 8b and 20 mol % of 4'-(5-butyldimethylsilylbutyloxypyrimidin-2-yl)phenyl 4-octyloxybenzoate has the following phase ranges:

X −8 S$_c$ 59 N 100 I.

The crystallization temperature at a cooling rate of 10° C. min$^{-1}$ is −30° C. If these phase ranges are compared with the phase range of the mixture 8b, it is found that adding the silyl component results in a lowering of the melting point by 4.5° C. and a lag in the crystallization temperature of 11° C.

APPLICATION EXAMPLE 22 a) In order to investigate the effect of the silyl pyrimidine compounds on the effective tilt angle, 10% of various components were dissolved in each case in the following ferroelectric mixture:

| | |
|---|---|
| 5-octyloxy-2-(4-hexyloxyphenyl)pyrimidine | 10.5 mol % |
| 5-octyloxy-2-(4-octyloxyphenyl)pyrimidine | 4.8 mol % |
| 5-octyloxy-2-(4-butyloxyphenyl)pyrimidine | 11.1 mol % |
| 5-octyloxy-2-(4-decyloxyphenyl)pyrimidine | 8.8 mol % |
| 4-(5-dodecylpyrimidin-2-yl)phenyl trans-4-pentylcyclohexanecarboxylate | 16.6 mol % |
| 5-octyl-2-(4-decyloxyphenyl)pyrimidine | 11.2 mol % |
| 5-octyl-2-(4-octyloxyphenyl)pyrimidine | 15.2 mol % |
| 5-octyl-2-(4-hexyloxyphenyl)pyrimidine | 16.8 mol % |
| 4-(2-octyloxypyrimidin-5-yl)phenyl (2R, 3R)-3-propyloxirane-2-carboxylate | 0.9 mol % |
| (R)-4-(5-n-octylpyrimidin-2-yl)phenyl 2,2-dimethyl-1,3-dioxolane-4-carboxylate | 4.1 mol % |

The structure of the components and the change in the contrast are shown in the following table.

The measurement results shown in Table I show that the use of silyl compounds (Examples: 22d, 22e, 22f) leads to an increase in the effective tilt angle compared with the analogous alkyl compounds.

TABLE I

Correlation between structure and contrast

| Example No. | Structure of the 10% mixture constituent in the mixture 17a | Effective tilt angle |
|---|---|---|
| 22a | pure basic mixture | 6.5 |
| 22b | $C_8H_{17}$—O—[pyrimidine]—[phenyl]—O—$C_8H_{17}$ | 8 |
| 22c | $C_9H_{19}$—O—[pyrimidine]—[phenyl]—O—$C_5H_{10}$—C(CH$_3$)$_3$ | 8.1 |
| 22d | $C_8H_{17}$—[pyrimidine]—[phenyl]—O—$C_6H_{12}$—Si(CH$_3$)$_2$—$C_2H_5$ | 8.5 |
| 22e | $C_8H_{17}$—O—[pyrimidine]—[phenyl]—O—$C_6H_{12}$—Si(CH$_3$)$_2$—$C_2H_5$ | 9 |

TABLE I-continued

Correlation between structure and contrast

| Example No. | Structure of the 10% mixture constituent in the mixture 17a | Effective tilt angle |
|---|---|---|
| 22f | $C_8H_{17}-O-\langle\langle N=N \rangle\rangle-\langle\langle \rangle\rangle-O-C_4H_8-Si(CH_3)_2-C_4H_9$ | 9 |

APPLICATION EXAMPLE 23 a) A mixture composed of the components

| | |
|---|---|
| 5-octyloxy-2-(4-hexyloxyphenyl)pyrimidine | 23.8 mol % |
| 5-octyloxy-2-(4-octyloxyphenyl)pyrimidine | 11.0 mol % |
| 5-octyloxy-2-(4-butyloxyphenyl)pyrimidine | 25.2 mol % |
| 5-octyloxy-2-(4-decyloxyphenyl)pyrimidine | 20 mol % |
| 5-octyl-2-[4-ethyldimethylsilylhexyloxy)-phenyl]pyrimidine | 20 mol % | has the following liquid-crystalline phase ranges:

X6.5S$_c$67S$_A$83N86I.

b) Compared therewith, the liquid-crystalline mixture claimed in DE 3,831,226.3, which differs from the above-mentioned mixture only in that it contains no silyl component, has the following phase ranges:

X5S$_c$68S$_A$83N86I.

c) A further comparison mixture contains 20% of the following component: 5-octyl-2-[4-(ethyldimethyl-silylhexyloxy)phenyl]pyrimidine, in the mixture 23b and has the following phase sequence:

X6.5S$_c$5.6S$_A$78I.

In the comparison with the mixture of Example 23a, it emerges that the position of the dimethylsilyl group has an effect on the melting point. A central position of the dimethylsilyl group in the chain is apparently more favorable.

APPLICATION EXAMPLE 24

A liquid-crystalline mixture is composed of the following components:

| | |
|---|---|
| 4'-hexyloxyphenyl 4-decyloxybenzoate | 22.0 mol % |
| 4'-hexyloxyphenyl 4-octyloxybenzoate | 26.8 mol % |
| 4'-undecyloxyphenyl 4-octyloxybenzoate | 16.2 mol % |
| 4'-(butyldimethylsilylbutyloxy)phenyl 4-decyloxybenzoate | 35.0 mol % |

X 25 S$_x$ 31 S$_c$ 63.5 S$_A$ 75 N 79 I.

The comparable mixture without silyl compound has the following phases:

X37.4S$_c$72S$_A$74N88I.

The silyl component therefore also results in a lowering of the melting point of 12° C. in a phenyl benzoate mixture.

APPLICATION EXAMPLE 25 a) A liquid-crystalline mixture composed of the following nine components

| | |
|---|---|
| 5-octyloxy-2-(4-hexyloxyphenyl)pyrimidine | 12.1 mol % |
| 5-octyloxy-2-(4-octyloxyphenyl)pyrimidine | 4.1 mol % |
| 5-octyloxy-2-(4-butyloxyphenyl)pyrimidine | 13.3 mol % |
| 5-octyloxy-2-(4-decyloxyphenyl)pyrimidine | 7.4 mol % |
| 5-octyl-2-(4-dodecylphenyl)pyrimidine | 10.8 mol % |
| 4-(5-decylpyrimidin-2-yl)phenyl trans-4-pentylcyclohexanecarboxylate | 17.2 mol % |
| 4-(5-octylpyrimidin-2-yl)phenyl heptanoate | 18.1 mol % |
| 4'-(butyldimethylsilylbutyloxy)phenyl 4-decyloxybenzoate | 17.0 mol % | has the following phase ranges:

X—16S$_c$60S$_A$75N84I

The crystallization temperature at a cooling rate of 10° C. min$^{-1}$ is —28° C.

b) To compare the physical properties, the phase ranges were measured of a mixture which differs from the above-mentioned one only in that it contains no silyl component. This comparison mixture has the following phase ranges:

X—9S$_c$73S$_A$77N96I.

The crystallization temperature under the abovementioned cooling conditions is —71° C. The silyl component apparently results in a lowering of the melting point and of the crystallization temperature.

APPLICATION EXAMPLE 26

A ferroelectric mixture is composed of
92.66 mol % of the mixture of Example 25,
4.02 mol % of 4-(2-octyloxyprimidin-5-yl)phenyl (2R, 3R)-3-propyloxirane-2-carboxylate, and
3.32 mol % of (S)-4-(2-octyloxypyrimidin-5-yl)phenyl
spiro(1,3-dioxolane-2,1-cyclohexan-4-yl)methyl ether
and has the following phase ranges:

X—19S$_c$*60S$_A$*73N*82I.

At a temperature of 25° C., the mixture has a spontaneous polarization of 10.5 nC/cm$^2$ and switches with a switching time $\tau$ of 102 μs at a field of 10 V/μm.

APPLICATION EXAMPLE 27

A liquid-crystalline mixture is composed of
60 mol % of the mixture 25b and
40 mol % of 4'-butyldimethylsilylbutyloxyphenyl 4-decylbenzoate
and has the following phase ranges:

X—29S$_c$48S$_A$71N73I.

The crystallization temperature at a cooling rate of 10° C. min$^{-1}$ is —39° C. The comparison with the data of the mixture 25b proves that the compound according to the invention results in a substantial lowering of the melting point and in a considerable reduction in the crystallization temperature in the mixture.

APPLICATION EXAMPLE 28

A liquid-crystalline mixture is composed of
80 mol % of the mixture 25b and
20 mol % of 4'-(5''-butyldimethylsilylbutyloxypyrimidin-2''-yl)phenyl 4-octyloxybenzoate
X—17 $S_c$ 58 N 101 I.

The comparison with the data of the mixture 25b proves that the silyl compounds according to the invention result in a lowering of the melting point in mixtures.

APPLICATION EXAMPLE 29

A ferroelectric liquid-crystalline mixture is composed of the following 6 components

| | |
|---|---|
| a) 5-Octyloxy-2-(4-butyloxy-phenyl)-pyrimidine | 24 Mol % |
| 5-Octyloxy-2-(4-hexyloxy-phenyl)-pyrimidine | 22,8 Mol % |
| 5-Octyloxy-2-(4-oxtyloxy-phenyl)-pyrimidine | 10,8 Mol % |
| 5-Octyloxy-2-(4-dexyloxy-phenyl)-pyrimidine | 19,2 Mol % |
| trans-4-Pentyl-cyclohexancarboxylic acid [4-(5-decyl-pyrimidin-2-yl)]-phenylester | 13,5 Mol % |
| (2S,3S)-2[4-(5-Butyldimethylsilyl-butyloxy-pyrimidin-2-yl)-phenyloxy]-methyl-3-butyl-oxirane | 10 Mol % |

X 6,3 $S_c$* 81 N* 98 I

The mixture has a $P_s$ of 26 nC.cm$^{-2}$ and a switching time of 174 μs (at 20° C.).

b) Compared therewith a liquid crystal mixture of DE 38 31 226, which differs from the inventive mixture only in not having a doping agent, show the following phase sequence: X 9 $S_c$ 84 $S_A$ 93 N 105 I. The inventive mixture has a melting point which is 3° C. lower than the melting point of the non-inventive mixture. This example shows that the silyl compounds are suitable doping agents in ferroelectric liquid crystal mixtures.

APPLICATION EXAMPLE 30

A mixture is composed of
80 Mol-% of the mixture of application example 25 b,
20 Mol-% 4(Butyldimethylsilyl)butyl[4-(5-(4-decylphenyl-1,3,4-thiadiazol-2yl)phenyl]-ether and has the following phase sequence:

X-11 $S_c$ 72 $S_A$ 83 N 93 I

Compared with the mixtures of application example 25 b this mixture shows that this silyl compound of the thiadiazole is suitable for a melting point depression.

APPLICATION EXAMPLE 31

A ferroelectric liquid-crystalline mixture is composed of
90 Mol-% of the mixture of application example 29 b,
10 Mol-% (2R,3R)-3-Propyl-oxiran-2-carboxylic acid-[4-(5-(4-butyldimethylsilylbutyloxy)-pyrimidine-2-yl)phenyl]-ester This mixture has at a temperature of 20° C. a spontaneous polarisation of 97 Nc.cm$^{-2}$ and a switching time of 67 μs (applied field 10 vμm$^{-1}$). Compared therewith a mixture containing 10% of (2R,3R)-3-propyloxiran-2-carboxylic acid-octyloxypyrimidin-2-yl phenylester and 90% of the mixture of example 29 b has a spontaneous polarisation at 20° C. of 37 Nc.cm$^{-2}$. A mixture containing the inventive silyl compound as a doping agent has a spontaneous polarisation which is 2.6 times higher than the spontaneous polarisation of the comparable mixture.

APPLICATION EXAMPLE 32 a) A mixture composed of the components

| | |
|---|---|
| 2-octyl-5-[4-decyloxyphenyl]-1,3,4-thiodiazol | 26,4 Mol % |
| 5-[4-trans-hexylcyclohexyl]-2-[4-decylphenyl]-1,3,4-thiodiazol | 33,6 Mol % |
| 4-(Butyldimethylsilyl)butyl-[4-(5-(4-decyl-phenyl)-1,3,4-thiadiazol-2-yl)phenyl]-ether | 40 Mol % | has the following liquid-crystalline phase sequence:

X 22 $S_c$ 116 I b) Compared therewith the liquid-crystalline mixture which differs from the above-mentioned mixture only in that it contains no silyl compound has the following phase ranges X 47 $S_c$ 111 $S_A$ 120

The silyl compound results in a lowering of the melting point of 25° C. in a mixture of thiodiazoles.

We claim:

1. A liquid-crystalline silyalkyl or silyalkenyl compound of the general formula (I)

$$R^1(-A^1)_j(-M^1)_k(-A^2)_l(-M^2)_m(-A^3)_n-G-\underset{\underset{R^8}{|}}{\overset{\overset{R^6}{|}}{Si}}-R^7 \quad (I)$$

in which
$R^1$ denotes straight-chain or branched alkyl or alkenyl (with or without asymmetrical carbon atom) containing 2 to 16 carbon atoms, it also being possible for one or two nonadjacent —CH$_2$—groups to be substituted by —O—, —S—, —CO—O—, or —O—CO— and for hydrogen to be replaced by fluorine, or one of the following radicals $A^1, A^2, A^3$ denote, identically or differently, 1, 4-phenylene in which 1 or 2 hydrogens may be replaced by fluorine, trans-1,4-cyclohexylene pyridine-2,5-diyl, pyrimidine-2,5-diyl, 1,3,4-thiadiazol-2,5-diyl, 1,3-dioxane-2,5-diyl, $M^1$, $M^2$ denote, identically or differently, CO—O, O—CO, CH$_2$—O, O—CH$_2$, G, G¹ denotes straight-chain alkylene containing 1 to 16 carbon atoms in which one or two nonadjacent —CH₂— groups may also be replaced by —O—, —O—CO—, or —CO—O—, with the proviso that Si is bound only to a carbon which has hydrogen and/or carbon as adjacent atoms, R², R³, R⁴, R⁵ denote hydrogen or a straight-chain alkyl containing 1 to 16, in which a —CH₂— group may also be replaced by cyclic alkyl containing 3 to 8 carbon atoms, R⁶, R⁷, R⁸ denote straight-chain alkyl containing 1 to 16 carbon atoms or cyclic alkyl containing 3 to 8 carbon atoms, j, k, l, m, n denote 0 or 1, with the proviso that j+l+n=2 or 3.

2. The compound as claimed in claim 1, wherein, in the general formula (I) the grouping $$(-A^1)_j(-M^1)_k(-A^2)_l(-M^2)_m(A^3)_n-$$

denotes:

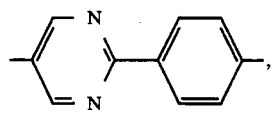,

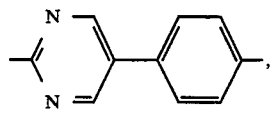,

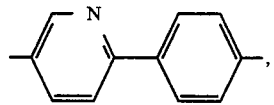,

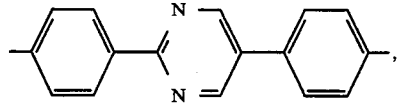,

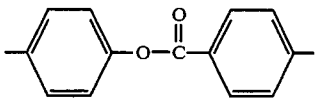

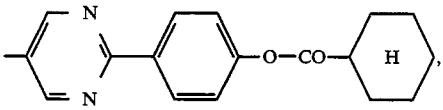,

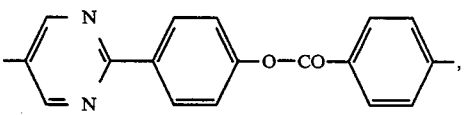, or

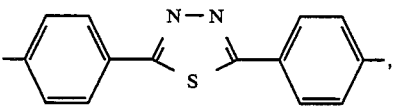,

3. The company as claimed in claim 2, wherein at least one of the radicals A¹, A², A³ denotes 1,4-phenylene and another denotes pyrimidine-2,5-diyl.

4. A liquid-crystalline mixture containing at least one silylalkyl or silylalkenyl compound of the general formula (I) as claimed in claim 1.

5. An electro-optic component containing a liquid-crystalline mixture as claimed in claim 4.

6. A liquid-crystalline mixture as claim in claim 4, wherein the liquid-crystalline mixture is nematic.

7. A liquid-crystalline mixture as claimed in claim 4, wherein the liquid-crystalline mixture is chiral nematic.

8. A liquid-crystalline mixture as claimed in claim 4, wherein the liquid-crystalline mixture is smectic.

9. A liquid-crystalline mixture as claimed in claim 4, wherein the liquid-crystalline mixture is chiral smectic.

10. A liquid-crystalline mixture as claimed in claim 4, wherein the liquid-crystalline mixture is ferroelectric.

11. 4-(Ethyldimethylsilyl)butyl 4-(2-octyloxypyrimidin-5-yl)phenyl ether.

* * * * *